United States Patent [19]

Newman

[11] 4,291,470

[45] Sep. 29, 1981

[54] METHOD FOR PRESHRINKING SEMIPERMEABLE MEMBRANES

[75] Inventor: Ferris E. Newman, Burlington, Vt.

[73] Assignee: Baxter Travenol Laboratories, Inc., Deerfield, Ill.

[21] Appl. No.: 42,367

[22] Filed: May 25, 1979

[51] Int. Cl.³ ............................................... F26B 1/00
[52] U.S. Cl. .......................................... 34/12; 34/23; 34/37; 34/60; 264/342 R; 264/342 RE
[58] Field of Search ................... 34/12, 23, 24, 28, 36, 34/37, 60, 68; 264/342 R, 342 RE

[56] References Cited

U.S. PATENT DOCUMENTS

| | | | |
|---|---|---|---|
| 1,482,717 | 2/1924 | Sulzer | 264/342 R |
| 2,062,193 | 11/1936 | Smith et al. | 34/24 X |
| 2,254,200 | 9/1941 | Ailes | 264/342 R |
| 2,364,467 | 12/1944 | Nickerson | 34/68 X |
| 2,459,345 | 1/1949 | Sisson | 34/23 |
| 2,770,053 | 11/1956 | Rosser et al. | 34/68 X |
| 2,934,400 | 4/1960 | Siggel et al. | 264/342 RE |
| 3,684,553 | 8/1972 | Van Dyk | 264/341 R |

FOREIGN PATENT DOCUMENTS 45-12992  11/1970  Japan .............................. 264/342 R Primary Examiner—Albert J. Makay
Assistant Examiner—Harold Joyce
Attorney, Agent, or Firm—Paul C. Flattery; Gerald S. Geren

[57] ABSTRACT

A method of preshrinking a semipermeable membrane or blood bag of the type used in an artificial-kidney coil dialyzer, so as to prevent or minimize shrinkage of the membrane during sterilization of the dialyzer. The preshrinking method of the present invention includes the steps of passing the membrane through a humidity chamber in a free-hanging state and then into a warm air drying chamber. The amount of membrane shrinkage can be controlled by varying the residence time, the temperature and the humidity of the chamber. By preshrinking the membrane to approximate the amount of shrinkage which normally occurs during the sterilization, substantially all shrinkage during sterilization is eliminated.

10 Claims, 1 Drawing Figure

METHOD FOR PRESHRINKING SEMIPERMEABLE MEMBRANES

FIELD OF THE INVENTION

This invention relates generally to semipermeable membranes for use in artificial kidney dialyzers, and more particularly, to a method of preshrinking membranes used in coil-type dialyzers.

BACKGROUND OF THE INVENTION

Artificial kidney systems are used to treat a patient's blood so as to remove waste products therefrom. One type of dialyzer used in such systems is commonly referred to as a coil dialyzer. It includes a flattened, tubularly-shaped, semipermeable membrane of a material such as cellophane or a regenerated cellulose derivative know as Cuprophan. A predetermined length of membrane is wound along with an appropriate support member about a center core which is then enclosed within a cylindrical housing. Blood from a patient enters the dialyzer through an inlet in the core, flows through the dialyzer inside the membrane and exits from the dialyzer through an outlet. Dialysis solution flows in a crosswise direction through the housing and between the wound support and membrane.

Dialysis solution contacts the membrane and due to the difference in waste product concentration between the blood and the dialysis solution, the waste products, such as urea and creatinine, diffuse from the blood, through the membrane and into the dialysis solution. Also, during treatment of the blood in the dialyzer, water is removed from the blood by virtue of a process known as ultrafiltration. The amount of water which is removed is related to the difference in blood pressure and dialysis solution pressure on opposite sides of the membrane.

After assembly, but prior to sale, the dialyzer is sterilized by flushing steam and a cleansing gas, such as ethylene tri-oxide (ETO), through the dialyzer at temperatures in excess of 120° F. The steam activates any bacteria in the dialyzer so that the bacteria will be destroyed when it takes on or reacts with the ETO. The steam provides a low humidity environment of less than 50% relative humidity.

It has been found that such sterilization causes the cellulose membrane to shrink. Due to the fact that the membrane and the support member may be wound snugly together about a dialyzer central core, shrinkage of the membrane may result in relative movement between the membrane and support member. This relative movement may result in rupture of the membrane and consequently cause the membrane to leak, thereby permitting undesirable blood leakage.

Further, the method by which the membrane is manufactured introduces stresses in the molecular structure of the cellulose material. Shrinkage due to the sterilization and those stresses may weaken the membrane and undesirably impair the consistency of its physiological properties.

In endeavoring to improve the characteristics of cellulose membranes for dialysis, researchers have attempted various types of water treatments. One such treatment involving the process of "water annealing" the membrane for the purpose of increasing hydraulic permeability was discussed in "Proceedings, Seventh Contractors' Conference of the Artificial Kidney Program", 1974, pps. 70, 73. Another water-related treatment suggested successively dampening and drying the cellulose membrane and noting the resultant dimensional changes to determine corresponding density changes (see "Transactions, American Society of Artificial Internal Organs,", Vol. XVI, 1970, pps. 115–120). However, no prior art exists which recognized the problem of cellulose membrane leakage occasioned by sterilization during manufacture.

It is accordingly the principal object of the present invention to provide a method of treating a semi-permeable membrane so as to minimize shrinkage during sterilization so as to, in turn, minimize subsequent damage to the membrane.

This and other objects and advantages of the invention will become clear from the following description of a preferred embodiment of the invention and appended claims.

SUMMARY OF THE INVENTION

A method of preshrinking cellulose semi-permeable membranes is disclosed herein which minimizes shrinkage of the membrane during sterilization and any resultant damage. In the method, a membrane is first passed through a humidity chamber for a period of time and at a temperature which is effective to produce a preselected amount of shrinkage. After leaving the humidity chamber, the moist membrane is supported in a free-hanging position and introduced into a warm-air drying chamber. It is believed that the cellulose membrane absorbs water from the humidity chamber, the result of which is to permit the membrane to relax, internal strains to be relieved and a molecular restructuring occurs. The drying chamber removes the water which has been absorbed without inducing any further changes in the molecular structure of the membrane. The dialyzer is then assembled, and during sterilization, the treated membrane experiences little, if any, additional shrinkage.

The membrane may be treated in chambers having between about 80–100% relative humidity, at temperatures between about 70° F. and 212° F., and for times ranging between 3 seconds and 70 hours. The resultant shrinkages have been between about 3% and 7%. However, it is believed that in commercially useful treatments the relative humidity will be about 100%, the temperature held between about 150° F.–212° F. and for times between 3 seconds and 10 minutes.

DESCRIPTION OF THE PREFERRED EMBODIMENT

Figure 1:
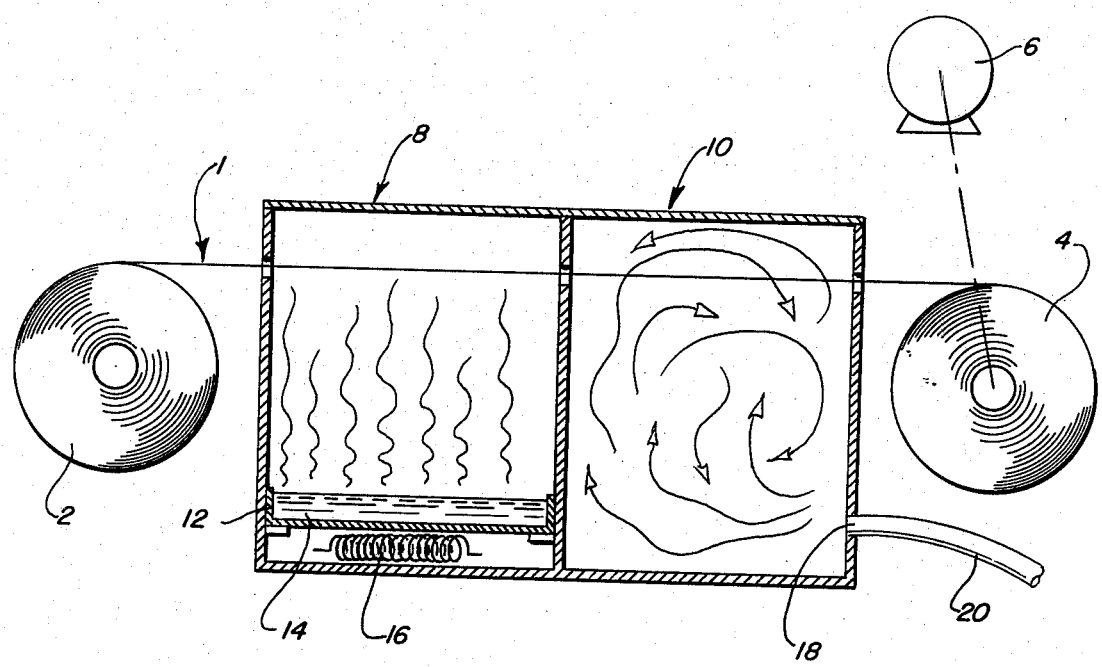
FIG. 1 is a schematic drawing showing the semipermeable membrane passing through adjacent humidity and drying chambers.

Referring now to the drawing, the semi-permeable membrane 1 is received on a supply spool 2. The free end of the membrane 1 is affixed to a spaced take-up spool 4 which is rotated at a very slow rate of speed by a drive motor 6.

As a membrane 1 moves from the supply spool 2 to the take-up spool 4, it passes first through a humidity chamber 8 wherein it absorbs water, and then into a drying chamber 10 wherein warm air circulates to dry the membrane 1. The only supports for the membrane are the spools 2 and 4, and the membrane 1 is maintained in a free-hanging condition within the chambers 8 and 10 so that it can shrink. If necessary, additional support rollers may be added as long as a major portion of the membrane 1 within the humidity and drying chambers 8 and 10 remains free-hanging. The membrane 1 is relatively unstressed during the wet and dry cycles.

The humidity chamber 8 includes a container 12 filled with a volatile liquid 14 (usually water) which is heated to a boil by any type of conventional heating means, such as coil 16. Warm air enters the drying chamber 10 through a slot 18 in the chamber wall or via a hose 20 or other similar conduit. Whether by a slot or hose, the air is supplied by any well-known type of warm air blower (not illustrated).

The semi-permeable membrane 1 is prepared from a tubular, semi-permeable regenerated cellulose-type packaging film sold under the name Cuprophan.

It should be appreciated that all of the chamber parameters, such as temperatures, time, relative humidity, etc., may be varied to control the amount of shrinkage.

It was experimentally determined that a 30-inch length of Cuprophan held in a humidity chamber maintained at 100% relative humidity and 75° F. for about 5 hours, shrink 5% along the length and 10% across the width. Those values approximate the shrinkage a membrane will actually experience during sterilization. After the preshrinking treatment, the Cuprophan membrane exhibits little or no change in length of width when the dialyzer is sterilized. This provides a dialyzer in which membrane movement relative to the support member has been minimized.

The membrane can be treated at temperatures as high as 212° F. Which will result in a decrease in the residence time in the chamber.

A relative humidity of 100% is easily obtained, and it is anticipated that any commerical system embodying this invention will employ a chamber operating at 100% relative humidity. However, relative humidities as low as about 80% may be employed.

Furthermore, in any commercial process it will be desirable to minimize the amount of time which the treatment requires. To this end, temperatures between about 150° F. and 212° F. will be employed which result in treatment times varying between 3 seconds and 10 minutes.

It should also be noted that since the invention is a vapor phase treatment, other volatile liquids besides water, such as mixture of water and immiscible liquids, such as xylol, trichlorethylene, ethyl acetate, ethyl alcohol or cyclohexane, may be used.

The following table sets forth a series of examples employing mixtures of water and other liquids as well as the test results. All examples were run at room temperature (75° F.) and 100 relative humidity:

| Liquid (In Volume %) | Time | Shrinkage |
|---|---|---|
| 50% H$_2$O<br>50% Ethyl Alcohol | 22 hrs. | 6.5% |
| 50% H$_2$O<br>50% Trichlorethylene | 24 hrs. | 5.0% |
| 50% H$_2$O<br>50% Ethyl Acetate | 6 hrs.<br>70 hrs. | 3.0%<br>6.0% |
| 50% H$_2$O<br>50% Cyclohexane | 3 hrs.<br>7 hrs.<br>22 hrs. | 3.3%<br>4.3%<br>7.0% |

From the foregoing it is seen that the time can vary between 3–70 hours and shrinkages obtained between 3%–7%.

While one preferred method of practicing the present invention has been described, it will be understood that the invention may be practiced by modified methods, so that the purpose of the appended claims is to cover all such variations of the preferred method not disclosed but which embody the method disclosed herein.

What is claimed is:

1. A method of treating cellulose semi-permeable membranes, of the type used in coil dialyzers, so as to minimize shrinkage of the membrane during sterilization of the dialyzer, the method including the steps of:
   providing a supply of cellulose semi-permeable membrane material;
   transporting said material from said supply through a humidity chamber maintained at a very high relative humidity, at a temperature and for a time effective to permit said material to relax; and
   passing said material into a drying chamber in which warm air is circulated for permitting the membrane material to shrink.

2. A method as in claim 1, wherein the relative humidity of the humidity chamber is maintained between about 80%–100%.

3. A method as in claim 2, wherein the relative humidity is maintained at about 100%.

4. A method as in claim 1, wherein the temperature in the humidity chamber is maintained at a value between about 70° F. and 212° F.

5. A method as in claim 4, wherein the temperature is maintained between about 150° F. and 212° F.

6. A method as in claim 1, wherein the time of treatment is between about 3 seconds and 70 hours.

7. A method as in claim 6, wherein the time of treatment is between about 3 seconds and 10 minutes.

8. A method as in claim 1, wherein said chamber includes a volatile liquid which is water.

9. A method of treating cellulose semi-permeable membranes, of the type used in coil dialyzers, so as to minimize shrinkage of the membrane during sterilization of the dialyzer, the method including the steps of:
   providing a supply of cellulose semipermeable membrane material;
   transporting said material from said supply through a humidity chamber maintained at a very high relative humidity, at a temperature and for a time effective to permit said material to relax;
   passing said material into a drying chamber in which warm air is circulated for permitting the membrane material to shrink; and
   wherein said humidity chamber includes a volatile liquid having between 50%–100% water and up to 50% of a liquid selected from the group ethyl alcohol, trichlorethylene, ethyl acetate and cyclohexane.

10. A method of pretreating regenerated cellulose semipermeable membranes of the type used in coil dialyzers so as to prevent shrinkage during subsequent sterilization, the method including the steps of:
   providing a supply of regenerated cellulose semi-permeable membrane material;
   transporting said material through a treatment chamber maintained at about 100% relative humidity and at a temperature between about 150° F.–212° F. for a time between 3 seconds and 10 minutes; and thereafter
   passing said material into a drying chamber in which warm air is circulated.

* * * * *